United States Patent [19]

Olofson et al.

[11] 4,161,597

[45] Jul. 17, 1979

[54] N-ALKYL-14-HYDROXYMORPHINANS AND DERIVATIVES

[75] Inventors: Roy A. Olofson, State College, Pa.; Joseph P. Pepe, Rochester, N.Y.

[73] Assignee: Research Corporation, New York, N.Y.

[21] Appl. No.: 751,571

[22] Filed: Dec. 20, 1976

[51] Int. Cl.² .................. C07D 489/08; C07D 221/28
[52] U.S. Cl. ......................................... 546/15; 546/44; 546/45; 546/74
[58] Field of Search ......................................... 260/285

[56] References Cited

U.S. PATENT DOCUMENTS

| 3,201,403 | 8/1965 | Sawa et al. | 260/285 |
|---|---|---|---|
| 3,320,262 | 5/1967 | Lewenstein et al. | 260/285 |
| 3,332,950 | 7/1967 | Blumberg et al. | 260/285 |
| 3,393,197 | 7/1968 | Pachter et al. | 260/285 |
| 3,828,050 | 8/1974 | Buckett et al. | 260/285 |

FOREIGN PATENT DOCUMENTS

| 913077 | 10/1972 | Canada | 260/285 |
|---|---|---|---|
| 65/22189 | 10/1965 | Japan. | |
| 1300419 | 12/1972 | United Kingdom. | |

OTHER PUBLICATIONS

Olofson, et al., Chemical Abstracts, vol. 87, 168234z (1977).
Olofson, et al., Chemical Abstracts, vol. 87, 168235a (1977).
Olofson, et al., Chemical Abstracts, vol. 87, 168236b (1977).

*Primary Examiner*—Donald G. Daus
*Assistant Examiner*—Diana G. Rivers
*Attorney, Agent, or Firm*—Omri M. Behr

[57] ABSTRACT

There is provided a novel and high yield procedure for transforming acid salts of 14-alkanoyloxymorphinans and derivatives thereof into the corresponding N-alkyl-14-hydroxymorphinans wherein the alkyl moiety on the nitrogen contains the same number of carbon atoms as that previously in the 14-alkanoyl moiety. In the process of the present invention, the acid is neutralized to the free base, the alkanoyl moiety at the 14-oxy then spontaneously shifts to the nitrogen and is subsequently reduced to the corresponding alkyl moiety. O-dealkylation at C-3, where an alkoxy group is originally present, is carried out in the usual manner. There is also provided a readily produced and readily disassociated adduct of the corresponding 14-hydroxy-N-alkanoyl morphinan-6-alkylene ketal with benzene, tetrahydrofuran, and the like.

17 Claims, No Drawings

N-ALKYL-14-HYDROXYMORPHINANS AND DERIVATIVES

BACKGROUND OF THE INVENTION (The invention described herein was made under Grant GM 13980 from the National Institutes of Health, Department of Health, Education and Welfare).

In Applicants' co-pending application Ser. No. 751,570, filed concurrently herewith there is disclosed a ready method for the N-dealkylation, suitably the N-demethylation, of N-alkyl-14-alkanoyloxymorphinans and their 3-alkoxy-(and acyloxy)-4,5-oxa, 6-keto, and 4,5-oxa-6-keto analogs, suitably of the oxycodone or oxymorphone series. The disclosure of said application is, for purposes of brevity, incorporated herein. It had been reported by currie et al (J. Chem. Soc. 4693 (1961)), that the 14-alkanoyl-N-cyanonoroxycodones and derivatives thereof could be rearranged to the corresponding N-alkanoylnoroxycodones in the presence of aqueous acid at reflux in moderate crude yields or in excess strong base (aqueous alcoholic KOH) at reflux in poor yield by somewhat involved procedures.

SUMMARY OF THE INVENTION

It is the surprising finding of the present invention that a 14-0 to N shift of an alkanoyl group can be caused to occur spontaneously in the free bases in the 14-hydroxymorphinan series. It is our surprising finding that the reaction is substantially instantaneous, occurs in high yields, and is caused merely by the dissociation or neutralization of the otherwise very stable corresponding acid salt to the free base, which then is rearranged in the aforesaid O-N shift.

It is a further surprising finding of the present invention that where it is desired to provide an alkyl group on the nitrogen by reduction of the aforesaid shifted alkanoyl group, and said reduction is to be attempted on a 6-alkylene ketal where the starting material has a keto group of the 6-position, said alkylene ketal forms a readily isolable adduct (not necessarily 1:1) with aromatic solvents such as benzene, alkyl substituted benzenes of 1-5 alkyl substituents such as toluene, xylene, mesitylene, tetrahydrofuran and alkyl substituted tetrahydrofurans of 1-4 substituents, and the like. This adduct, because of its very low solubility in the cold solvent and high solubility in the hot solvent, provides a simple and rapid method of purification since the solvent may be readily and totally removed therefrom under reduced pressure and moderately elevated temperatures. Moreover, this sovlent of crystallization generally does not interfere in the subsequent reduction step so the adduct may be used directly in that process. It should be noted that these solvent adducts may sometimes be stoichiometric (i.e. 1:1 molecule ratio), but such adducts are the exception rather than the rule and the invention is not limited thereto.

It has also been found that where said newly prepared N-alkylated 14-hydroxymorphinans are prepared from the corresponding 3-alkoxy derivative, the alkyl group at the 3-oxy position is readily removed by known procedures to provide desired compounds such as nalbuphine as well as its immediate precursor N-cyclobutylmethylnoroxy morphône and naltrexone -- the first in yields higher than that heretofore obtainable, and the latter in yields which, though higher than heretofore obtainable, are competitive to those obtained by the alternate procedures set forth in Applicants' co-pending application filed herewith. Part of the yield advantage of our process arises surprisingly from the fact that in our process N-alkylation is carried out before 3-dealkylation whereas the prior art teaches 3-dealkylation prior to N-alkylation.

Although it has heretofore been possible to carry out a direct alkylation of, say, noroxycodone, the yields obtained in said process are usually considerably inferior to those obtained in the present, though lengthier process. Flow sheets of the procedures of the present invention are set forth hereinbelow. It should be noted, however, that the specific examples a through c, e and f, set forth therein are purely illustrative of certain preferred embodiments of the present invention and are in no way to be considered as limiting thereof.

It should further be noted that while in the nitrogen containing ring of the morphinans of the present invention, certain bonds and the hydroxyl attached thereto are shown in the β-orientation, the mirror image, optical isomer, or α-orientation, as well as mixtures of both forms are included in the scope of the present invention.

It should also be noted that in the discussion which follows, compounds wherein $R_2$ with $R_3$ is oxa and Q is oxo (see Flowsheet I) are sometimes referred to as being in the "natural series" because some though not all of these compounds are conveniently derived from oxycodone or oxymorphone. Compounds wherein $R_2$ and $R_3$ are each hydrogen are often referred to as being in the "synthetic series" because their normal precursors are usually though not always made by more involved routes from smaller compounds.

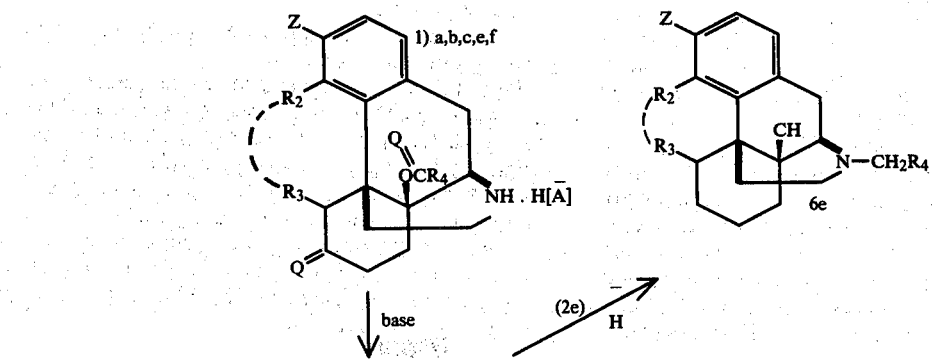

FLOWSHEET I

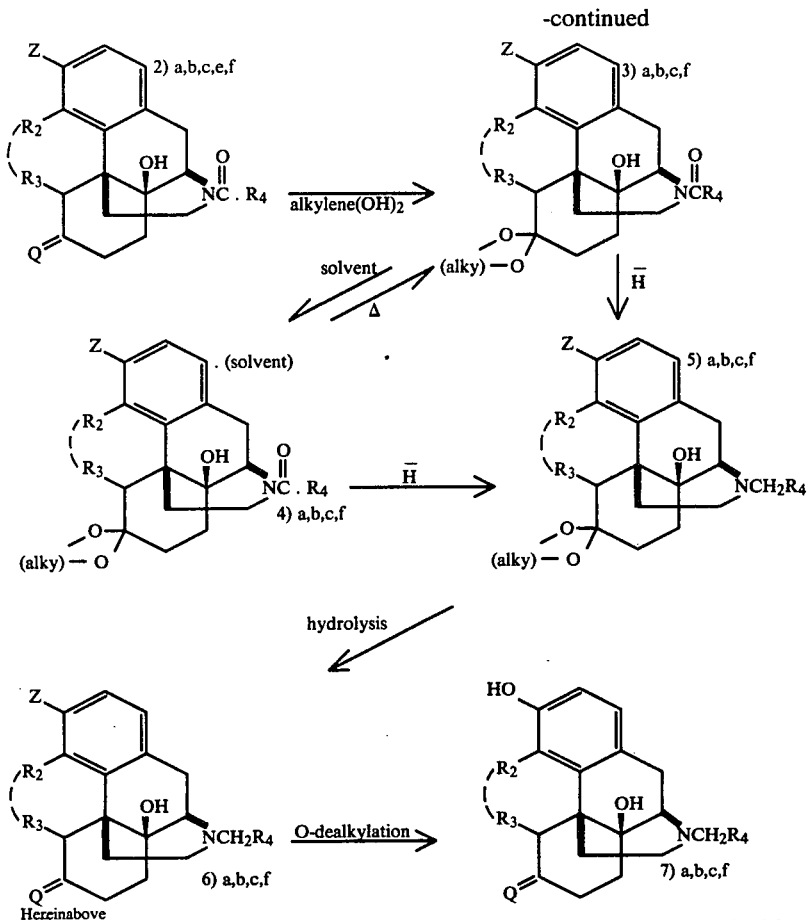

Hereinabove
H(A) is the hydrogen acid capable of forming a salt with a secondary amine, Q is O for a,b,c, and f, and (H,H) for e; $\overline{H}$ is a reducing agent; Z is $R_1O$, $R_1$ is methyl, $R_2 + R_3$ = oxa for a,b,c and $R_2 = R_3$ = H for e and f; $R_4$ = Cp = cyclopropyl for a, e; $R_4$ = Cb = cyclobutyl of b and f and $R_4$ = methyl for c; (alky) = alkylene of 2–5 carbon atoms.

DESCRIPTION OF THE PREFERRED EMBODIMENTS

In the preferred embodiments of the present invention Z is hydrogen or $R_1O$ where $R_1$ is alkanoyl, benzoyl, phenylalkanoyl, substituted benzoyl/or phenylalkanoyl, suitably alkyl- or polyalkyl-benzoyl or -phenylalkanoyl, cycloalkylcarbonyl, or alkyl, cycloalkyl or alkylcycloalkyl; $R_2$ and $R_3$ may each be hydrogen or when taken together are oxa; Q is 2 hydrogen atoms or oxo; $R_4$ is hydrogen, alkyl, cycloalkyl, alkylcyclo-alkyl, phenyl or substituted phenylalkyl such as alkyl- or polyalkylphenyl.

In the process of the present invention, there may, suitably, be used any 3-acyloxy or 3-alkoxy-14-acyloxymorphinan salts produced from the corresponding N-alkyl-14-hydroxymorphinans in accordance with the procedures of our co-pending application filed on even date herewith, the disclosure of which is incorporated by reference. $R_1$ may be formyl, alkanoyl, suitably lower alkanoyl -- for example, having 1 to 5 carbon atoms in the alkyl moiety thereof -- for example, acetyl, propionyl, butyryl, valeryl, and the like, benzoyl, phenylalkanoyl and substituted phenylalkanoyl suitably phenyl lower alkanoyl such as phenylacetyl, phenylpropionyl, phenylbutyryl, and the like, and as substituted phenyl lower alkanoyls may be included, moieties having — for example, alkyl substituents in the phenyl nucleus, also included is cycloalkylcarbonyl such as cycloloweralkylcarbonyl of 3 through 6 carbon atoms in the cycloalkyl moiety, including in particular cyclopropyl and cyclobutyl.

$R_1$ may be alkyl, suitably lower alkyl of 1 to 5 carbon atoms such as methyl, ethyl, propyl, butyl and the like, or benzyl or phenylalkyl such as phenethyl, phenylbutyl, and the like. [$\overline{A}$] is the anion of any proton acid capable of forming an acid addition salt with a secondary amine, included are the anions of mineral acids such as halo, suitably chloride or bromide, sulfate, nitrate, phosphate and the like, the anions of organic acids such as carboxylic or lower alkanoic acids such as formate, acetate, propionate and the like, and anions of sulfonic acids, suitably arylsulfonic acids such as benzene or toluene sulfonates and of alkyl sulfonic acids such as methane sulfonate.

The foregoing list is not intended to be exhaustive or limiting but merely exemplary.

$R_2$ and $R_3$ are each hydrogen or when taken together are oxa, Q is either 2 hydrogen atoms or oxo. Thus, in the synthetic morphinan series, $R_2$, $R_3$ and Q are all originally hydrogen though Q may also be oxo and in the natural series $R_2$ with $R_3$ is oxa, and Q is oxo. Among the most important starting materials may be mentioned oxycodone which is utilized in the naltrexone synthesis as well as in the nalbuphine synthesis.

Any readily available and desired acyl group on the 14-oxygen may constitute a

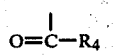

group. The carbonyl moiety thereof will be reduced as set forth hereinbelow to yield the corresponding substituted methyl group, $CH_2R_4$. Thus, for example, where

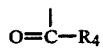

is acetyl, $CH_2R_4$ will be ethyl, or where

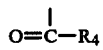

is cyclopropylcarbonyl, $CH_2R_4$ wll be cyclopropylmethyl. $R_4$ may be lower alkyl moiety having 1 to 5 carbon atoms; it may also be phenyl, a phenyl lower alkyl moiety, suitably benzyl; also included are cycloalkyl and lower alkyl cycloalkyl moieties having from 3 to 6 carbon atoms in the cycloalkyl moiety and 1–5 carbon atoms in the lower alkyl moiety. Where it is desired to proceed further to the synthesis of nalbuphine or naltrexone, there is employed as the alkanoyl group cyclobutylcarbonyl or cyclopropylcarbonyl.

When an original starting material is an N-alkyl-3, 14-dihydroxymorphinan (e.g., oxymorphone), then $R_1$ in compounds (1) – (4) will often be

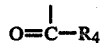

because of the convenience of using the same acylating agent to react with the 3 and 14 hydroxyls. Then in compound (5), $R_1$ would be hydrogen.

In the rearrangement process of the present invention, Flowsheet I, the 14-alkanoyloxymorphinan acid salt (1) — for example, the salt of a mineral acid, suitably a hydrohalic acid such as hydrogen chloride or alkanoic acid such as acetic acid — is taken up in a substantially water insoluble reaction inert polar organic solvent with a comparatively low tendency to emulsify with aqueous base. Among the most desirable solvents are halogenated hydrocarbons and among these, methylene chloride and chloroform are especially preferred. Also preferred are esters such as ethyl acetate.

As stated heretofore, the rearrangement reaction will occur extremely rapidly upon neutralization of the acid salt, hence, although any base may be used to neutralize the salt, suitably inorganic bases to lower the possibility of emulsification, it is preferred to use the mildest of inorganic bases. Especially preferred is saturated aqueous sodium bicarbonate. The invention is, however, in no way limited thereto.

The salts of weak acids such as alkanoic acids with any metals, suitably alkali metals, alkaline earth metals, and transition metals, may be employed. Especially favored, where for example, the acid salt is the hydrochloride, are the silver salts of alkanoic acids such as silver acetate. Stronger bases such as alkali metal hydroxides, suitably sodium hydroxide or potassium hydroxide, alkaline earth metal hydroxides, such as calcium hydroxide, barium hydroxide, and the like, as well as ammonium hydroxide or carbonates such as sodium carbonate, potassium carbonate, or calcium carbonate, may also be employed. Where the acid salts are the salts of weak acids, such as alkanoic acid salts, or the like, a base as weak as water is sufficient to cause dissociation and rearrangement. Under such circumstances it is preferred, but not critical to heat the aqueous solution of the acid salt. Heating to between about 40° and 70° C. is adequate. Under the conditions where stronger bases are utilized, it is advisable, although not critical, to carry out the basification step, utilizing a pH meter so that the pH does not rise much above pH 11, pH 8 – pH 9 being especially preferred.

In an especially preferred modification of this step the 14-alkanoyloxy acid salt (1), is suspended in the selected organic solvent and shaken vigorously with aqueous saturated bicarbonate. The reaction may be most conveniently carried out at ambient temperatures, and is considered complete when the suspended material is dissolved. Depending on the vigor of the shaking process, the reaction time may be between one and thirty minutes; however, the reaction should generally be considered as complete in about five minutes. The mixture is permitted to settle, the organic layer removed, the aqueous layer reextracted, the organic layers combined, washed with water, and dried to form the desired 14-hydroxy-N-alkanoylmorphinan (2). This compound may, if desired, be purified; however, the material produced in this reaction is of adequate purity to proceed directly to the next step of the reaction.

In another especially preferred modification of the step (1) – (2), the acid salt (1) is dissolved in a lower alkanol, suitably methanol or ethanol. Then an equivalent of an anion exchange resin in the hydroxide form is added; the mixture is shaken for five to ten minutes, then filtered to remove the resin. Simple solvent evaporation from the filtrate then yields the N-alkanoylmorphinan (2).

As stated heretofore, it is contemplated that the compounds of formula (1), that is to say, the N-desalkyl-14-acyloxy salts will be prepared and isolated in accordance with the procedures set forth in our copending application filed concurrently herewith. The invention is not so limited however. The 14-hydroxy-N-acyl compounds (2) of the present invention may be prepared without isolation of purified intermediates.

The general procedure for such a partial reaction sequence is summarized (but not detailed) on Flow Sheet II. In the steps 8 through 9' or 9'' the N-alkyl group is replaced by a desalkylating group either ($\overline{TOC}$) in (9') or ($\overline{YOC}$) in (9''). The desired N-acyl product (2) is obtained by dissociation of the N-($\overline{TOC}$) (9') or N-($\overline{YOC}$) (9'') product followed by rearrangement to the desired product (2). It has been found that once dissociation occurs, rearrangement is very rapid.

The dissociation of the N-($\overline{TOC}$) grouping may be carried out directly or indirectly in varying degrees of efficiency, depending on the combination of reaction parameters selected. It is preferred to treat the N-($\overline{TOC}$) compound with an electron donor, although base treatment is also operative. Especially preferred as an electron donor is metallic zinc in the presence of a protic solvent, zinc/copper couple or similar electron source may also be employed. Also included as an electron donor is the cathode of an electrolytic cell.

When metallic zinc is the electron donor there may be employed as a solvent, a lower alkanoic acid, preferably acetic acid, a lower alkanol such as methanol or ethanol. These solvents are preferably used in the presence of water. Other reaction inert water miscible co-solvents may also be used in the presence of water. Such solvents include, but are in no way limited to, dioxan, glyme, ethylene glycol, tetrahydrofuran, and the like.

Where the reaction is carried out in an alkanoic acid there is formed (but not purified) the O-acyl-NH alkanoic acid salt which then may be dissociated. The dissociation and subsequent rearrangement may occur merely by removing the solvent under reduced pressure and, suitably, heating the product as well. High temperatures are not required; temperatures up to steam bath temperatures are adequate. Most suitably, however, dissociation will take place upon treatment of the residue with base.

In the foregoing modification where the residue, after the removal of the solvent, is heated, it is generally preferred to carry out the heating in a solvent of moderate boiling point, say a solvent having a boiling point of between about 80° and 150° C. Heating at temperatures between 40° C. and reflux is satisfactory. The solvent is then removed after heating to leave the desired product as a residue.

Where, say, zinc treatment is carried out in a non-acidic solvent such as in alkanol, it is preferred to add a small, catalytic, amount of acid, preferably, but not limited to, mineral acid, say 0.1 equivalent per equivalent of O-acyl-N-(TOC) compound, to initiate the dissociation which proceeds upon heating, suitably at reflux temperature of the solvent to provide the rearranged N-acyl compound (2) with the exception of the small amount present in the form of the O-acyl-NH acid salt.

However, where a larger amount of acid, say mineral acid, suitably about one equivalent of mineral acid is employed, the (TOC) group is more rapidly removed.

In this modification the residue is in the form of a mineral acid salt which is substantially more stable than the alkanoic acid salt. Thus for practical purposes the rearrangement to the N-acyl compound (2) would require treatment with base to provide significant yields. Any of the bases set forth hereinabove may be employed.

In all of the foregoing procedures the zinc salts formed may suitably be removed by treating the mixture of N-acyl compound (2) and zinc salt with an aqueous base of moderately high pH aqueous alkali of pH 11 to 12 being especially suitable. Such an aqueous solution will dissolve the amphoteric zinc hydroxide intermediately formed.

Where the N-desalkylating agent gives rise to either (YOC) or (TOC) groups, suitably the vinyloxycarbonyl, (VOC) phenoxycarbonyl, (POC) or trichloroethoxycarbonyl, (TOC) the thus obtained compounds (9' and 9'') may be treated with base directly. Equimolar amounts or a slight excess of alkali, suitably aqueous alkali, such as sodium hydroxide, most suitably in a water miscible inert solvent such as glyme or dioxane, are added. Most suitably the reaction is carried out in an inert atmosphere, suitably a nitrogen atmosphere at ambient to moderately elevated temperatures—suitably between 20° C. and 80° C., preferably about 60° C. The reaction is run for from about 2 to about 40 hours, suitably about 4–8 hours, and quenched by reduction of alkalinity. Water and acids may be used. Another convenient method involves passing gaseous carbon dioxide through the reaction mixture. The O-acyl free amine generated directly in these base hydrolyses, spontaneously rearranges to (2). It should be noted however that while direct base treatment is the preferred mode of removal of (YOC) groups, it is preferred to remove the (TOC) group by the other procedures detailed immediately hereinbefore.

FLOWSHEET II

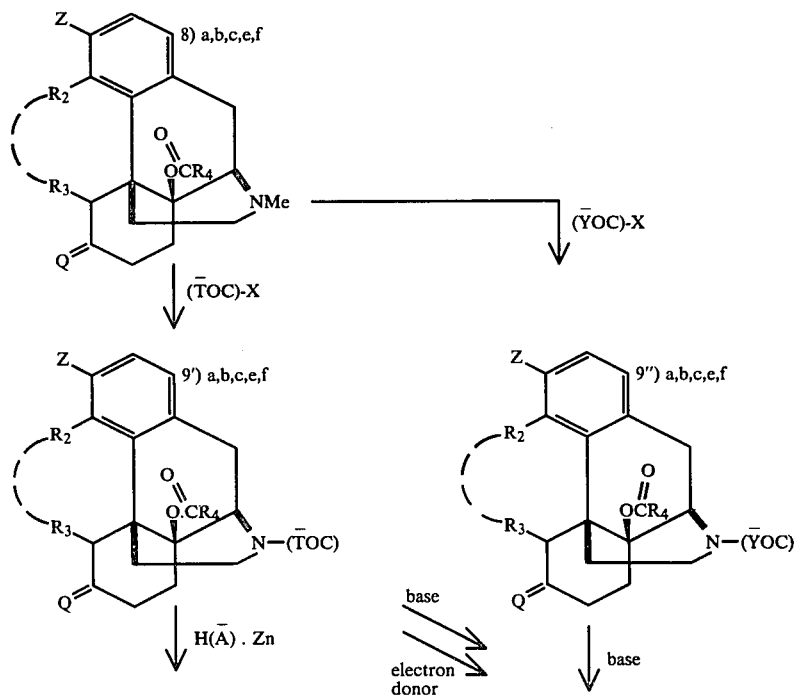

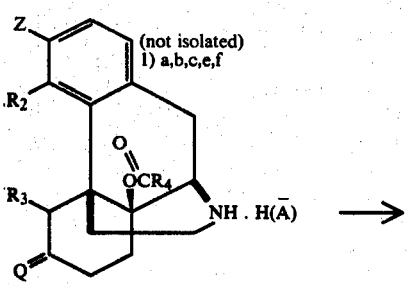
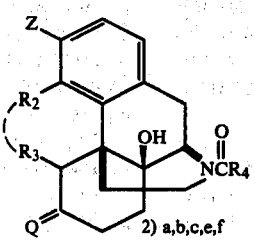

-continued

Hereinabove

H(A) Z, R$_2$, R$_3$, R$_4$, and Q are as in Flowsheet I. (TOC) is haloalkoxycarbonyl wherein haloalkoxy is 2-haloethoxy, 2,2-dihaloethoxy, or 2,2,2-trihaloethoxy, (TOC) where halo is chloro or bromo; (YOC) is vinyloxycarbonyl, (VOC) phenoxycarbonyl(POC) substituted phenoxycarbonyl wherein the phenyl substituents may be one or two chloro, bromo, nitro, or lower alkyl groups. X is chloride or bromide.

The products (2) from the various Flowchart II reaction series are then worked up. Work up may involve removal of all solvent (aqueous and other) under reduced pressure from the slightly to moderately basic mixture followed by extraction with a water immiscible polar organic solvent or involve direct extraction with such a solvent.

In the next stage of the reaction, the N-alkanoyl group is reduced to the corresponding alkyl group. Where the substituent at C-6 is hydrogen, this reduction may be carried out directly by means discussed in more detail hereinbelow. However, since the route to most, though not all, compounds producible by the present process lies through intermediates having a 6-keto moiety, the protection of said moiety and the consequences thereof will be discussed first.

The 6-keto group is protected by any suitable ketone protecting moiety which is resistant to reducing agents. It has been found most suitable to form ketals, suitably, single alkoxy ketals or cyclic ketals having 2 to 6 carbon atoms in the alkylene moiety, most suitably, ethylene ketal. If desired, the corresponding 6-enol ether may also be utilized as the protecting group. It should be noted however, that where the protecting agent is derived from a monohydric alcohol, the protected product may be either the 6-enol ether or the 6,6-diether (i.e. the "open" ketal). Which of these products is formed is of no great importance (see Flowsheet III).

It is also possible to permit the 6-keto group to be reduced to a 6-hydroxy which is subsequently reoxidized by methods well known in the art - e.g. by means of the Jones reagent (Chromium trioxide in pyridine). While this mode is included in the scope of the invention, it is not an especially preferred embodiment thereof.

FLOWSHEET III

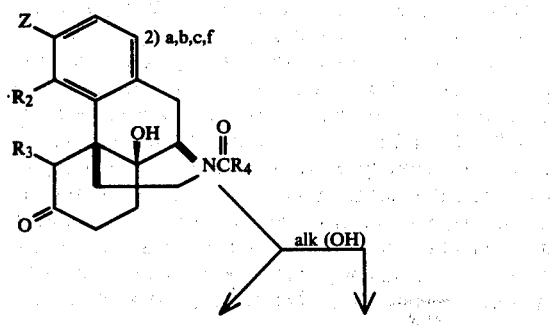

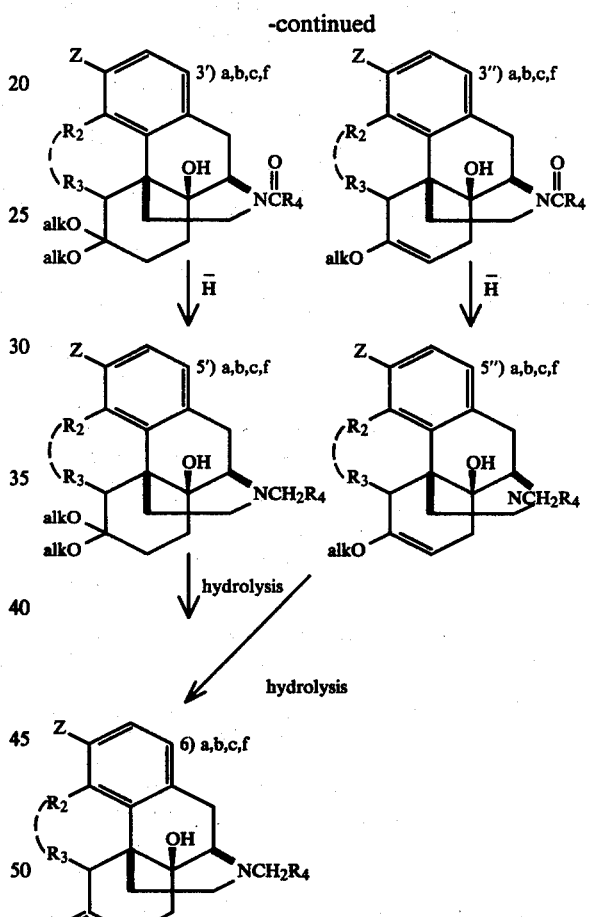

hereinabove Z = R$_1$O, alk = alkyl of 1-5 carbon atoms in a,b,c, and f, R$_1$ = CH$_3$;
in a,b, and c R$_2$ + R$_3$ = O, in f, R$_2$ = R$_3$ = H
in a, R$_4$ = C$_p$, in b and f, R$_4$ =Cb, in c R$_4$ = CH$_3$.

In the preferred modification concerned with the preparation of the ethylene ketal, the N-alkanoylmorphinan (2) is taken up in benzene or an alkylated benzene such as toluene, xylene, mesitylene, or the like in the presence of a substantial excess, suitably a tenfold excess, of ethylene glycol and a trace of a strong acid catalyst. As is well accepted in the formation of ketals, toluene sulfonic acid is a particularly effective catalyst. The reaction mixture is vigorously agitated and heated, most suitably under reflux until tlc analysis indicates little or no starting material remains. This may take for from about twelve to eighty or more hours, suitably for about thirty-six hours. The reaction may be accelerated with minimal sacrifice in product yield by increasing the amount of catalyst. During this procedure, the water formed in the course of the reaction is continuously removed, suitably by means of a Barret moisture test receiver or the like.

After completion of the reaction, the reaction mixture is cooled, quenched with mild base, suitably saturated aqueous sodium bicarbonate, diluted with water, and hot benzene, or one of the other aromatic solvents named above — if benzene, as close to its boiling point as feasible — is added to the mixture which is vigorously shaken and the aqueous layer removed. The volume of benzene utilized is approximately equal to that in which the reaction initially took place. After separation, the aqueous layer is then reextracted in a similar manner with hot benzene, the organic extracts combined, and washed with water — preferably warm water, most suitably water of a temperature of between 60° C. and 75° C. The organic extracts are then dried, suitably over potassium carbonate, and removed under reduced pressure to yield a residue which is readily recrystallized from hot benzene. The ketal (3) formed in the present reaction has a ready propensity to form an adduct with the solvent, and said adduct crystalizes very rapidly from the solvent at ambient temperatures. Thus, in order to reduce the amount of solvent required to carry out the extraction to the economically most efficient amounts, the extractions should be carried out in such a manner as to maintain the temperature of the organic solvent as high as is practical. This will, of course, cause certain problems with manipulation due to the high vapor pressure; however, this can be regulated in manners well known to those skilled in the art. The thus formed adduct, which is not necessarily a stoichiometric adduct, (with benzene, toluene, xylene, mesitylene or the like, whichever is used as the solvent) (4) crystalizes from the solvent in good yields at extremely high levels of purity. The adduct is very stable at ambient temperatures; however, at reduced pressure and elevated temperatures, suitably at pressures of less than 1 mm of mercury and temperatures in excess of 90° C., the solvent of crystallization is readily lost, usually in a period of between eight and eighteen hours. This method of purification has been found especially desirable.

In an alternate mode of purification, employing the same principles, the quenched, i.e. now aqueous, reaction mixture is extracted with a reaction inert substantially water immiscible solvent which is heavier than water - chloroform or methylene chloride being particularly suitable. This is advantageous in industrial procedures since the desired solvent may be readily run off from the bottom of the separation vessel.

The extract is then dried in the usual manner and the solvent removed, suitably under reduced pressure. The residual material is then treated with any of the aromatic solvents listed above, tetrahydrofuran or alkyl substituted tetrahydrofuran. In this procedure it is usually not necessary to heat this second solvent. The solvent is discarded and the residual material is the ketal-solvent adduct in crystalline form in sufficient purity for use in the next stage of the process.

Where it is desired to produce the 6-enol ether (3"), the corresonding compound (2) is preferably taken up in a suitable alkanol — for example, in methanol — and heated with the corresponding trialkylorthoformate, in the case of methanol, the trimethylorthoformate, in the presence of a trace of acid such as toluene sulfonic acid. There is utilized an excess of the trialkylorthoformate, suitably an excess of approximately 0.5 moles per mole. The reaction is carried out, suitably under an inert atmosphere under anhydrous conditions under reflux for from about twelve to about twenty-four, suitably about eighteen hours, at a temperature slightly below the boiling point of the solvent. At the completion of this period, the temperature is slowly raised, say, over a period of from about two to about four hours, to the boiling point of the pure solvent. The solvent and all other volatiles are thus slowly distilled off to yield the desired enol ether which is then purified in the usual manner.

To produce the simple ketal (3'), it is usually sufficient to take the above reaction mixture prior to the final solvent distillation, add some of the alkanol, suitably ten to twenty equivalents, - in the above Example, methanol - and continue to reflux for another one to two hours. Next, the acid catalyst is neutralized with base, suitably excess solid sodium carbonate, prior to the final distillation of the solvent and other volatiles.

The N-acyl-14-hydroxy morphinan protected, where required, at the 6-position, unless no keto group was originally present there, (3) is then reduced to the corresponding N-alkyl compound (6) by methods which are generally accepted in the art. In the preferred modification, the N-acyl compound (3) is taken up in a suitable reaction inert solvent, suitably an ethereal solvent, preferably dry tetrahydrofuran (rather than diethyl ether due to higher temperatures available) or dioxane, and is slowly added to a suspension of a reducing agent, such as lithium aluminum hydride or the like in a similar solvent. There is utilized a substantial excess of the reducing agent, an excess of between 1 and 3 moles per mole is generally preferred. The addition is carried out slowly, and under an anhydrous inert atmosphere, suitably under a nitrogen atmosphere. The addition is suitably completed in from about fifteen to about sixty minutes under reasonable agitation, and the reaction mixture left at ambient temperatures, suitably from about 15° to 25° C., for from about twelve to about twenty-four, suitably for about eighteen, hours. The reaction is then brought to completion by heating under reflux, suitably for about thirty minutes to about two hours, cooled, and quenched. The quenching is suitably achieved by the addition of water, followed by aqueous base, suitably aqueous sodium hydroxide. This mode of quenching is especially desirable since it gives rise to solid "waste" residues rather than emulsions. The solids are separated by filtration, the filrate retained, and the solids washed with fresh tetrahydrofuran, which is combined with the initial filtrate, and the combined filtrates evaporated under reduced pressure to give the desired N-alkyl-14-hydroxymorphinan (5).

The protecting moiety is then removed (where the protecting moiety is not present, the following steps are, of course, unnecessary). Where the protecting group is a ketal group, the immediately foregoing product is taken up in dilute mineral acid, suitably in aqueous hydrochloric acid of from about 0.5 N to about 5 N suitable about 1 N, and warmed at a temperaure of between about 80° C. and 95° C. (external) for from about one to about three, suitably about two, hours. The reaction mixture is made basic, suitably by the addition of concentrated aqueous ammonium hydroxide and extracted with a suitable reaction inert water immiscible polar organic solvent, suitably halogenated hydrocarbon solvent such as chloroform. The extract is then dried and the solvent removed to yield the corresponding N-alkyl-14-hydroxy-6-oxomorphinan (6) which may, if desired, be recrystalized. Where the protecting group is an alkyl enol ether, the protecting moiety is removed in a similar manner to yield the same desired end product. The N-alkyl-14-hydroxy-3-alkoxymorphinan (6) produced in accordance with the foregoing procedures is then O-dealkylated, suitably by reaction with pyridine hydrochloride or cold boron tribromide.

Alternatively a keto group in the 6-position of (3) may be left unprotected. Then it will be reduced to a hydroxy function during the lithium aluminum hydride treatment and must subsequently be reoxidized by known methods of the art to give (6).

In the foregoing discussions of the preferred experimental procedure, reference has been had principally to compounds carrying an alkyl group at $R_1$.

As stated heretofore, the procedure is also operative where $R_1$ is acyl. It will be readily understood that when $R_1$ is acyl, it will often have the same value as $R_4$. In the reduction step from Compound (3) to Compound (5), a modification wherein $R_1$ is acyl will be reduced to give a compound wherein $R_1$ is hydrogen. (If $R_1$ is an active acyl it may even be removed partly or completely by transesterification during the earlier ketalization step). In such a modification, the compound produced in the immediately preceding step (i.e. formation of Compound (6)) would not need to be subject to the O-dealkylation procedure set forth hereinbelow.

In the preferred dealkylation procedure, the N-alkyl-14-hydroxy-3-alkoxymorphinan (6) is mixed with the acid halide of a tertiary amine, suitably an aromatic tertiary amine, preferably pyridine, most suitably pyridine hydrochloride. An excess of the amine salt is utilized, most suitably an excess of between 5 and 15 moles per mole, preferably about 10 moles per mole. The reaction mixture is heated in an inert atmosphere, suitably a nitroen atmosphere, to a temperature of about 190° C. and left at that temperature for 10 to 30 minutes, suitably 20 minutes. The temperature is then raised another 5° to 20° and left at that temperature several minutes, suitably 5 to 10 minutes. The reaction mixture is then cooled, quenched with water, and made basic, suitably with concentrated aqueous ammonium hydroxide. This basification gives rise to a precipitate which is taken up in a suitable water immiscible reaction inert organic solvent, preferably in ether. The organic extract is then washed with strong (i. e., circa pH 13) aqueous alkali, suitable aqueous sodium hydroxide, and then with water. This procedure extracts the desired phenolic product into the strongly alkaline solution, leaving the unreacted 3-alkoxy compound in the ether layer, from which it can be recovered and recycled. The pH of the aqueous extract is then dropped to between pH 8 and ph 9, suitably to about pH 8.8 by the means of aqueous mineral acid whereby the desired product is precipitated from the aqueous solution and is then extracted with a water immiscible reaction inert organic solvent, suitably a halogenated hydrocarbon solvent such as methylene chloride or chloroform. The extract is then washed, dried, the solvent removed under reduced pressure, and the residue is further purified, suitably by short column silica gel chromatography. If desired, the thus produced 3,14-dihydroxy-N-alkylmorphinan (7) may be further purified by crystalization.

The foregoing discussion has been directed to experimental procedures involving substrates having a hydroxy group at the 3-position which may be alkylated or acylated prior to the processes of the present invention. The invention however is not limited thereto and morphinans which are not oxygenated at 3 are specifically considered to be within the scope of the present invention.

In the reaction sequence involving such substrates similar reactions and reagents are employed to provide the 14-hydroxy-N-acylmorphinans (2) either from the 14-acyloxymorphinan acid salt (1) or directly from the 14-acyloxyoxycarbonyl (i.e. VOC-,TOC- or POC-) derivative. Clearly, using such substrates, the O-dealkylation step (6) - (7) would be superfluous.

In the following Examples, all temperatures are in °C. Silica Gel $GF_{254}$ plates with 90% methylene chloride-10% methanol (v/v) as the eluant were used for all tlc analyses to obtain the $R_f$ reference values.

EXAMPLE I

N-ACETYLNOROXYCODONE (2c)

A suspension of 14-acetylnoroxycodone hydrochloride (1c) (1.14 g, 0.003 mole) in methylene chloride (15 ml) was vigorously shaken for 10 minutes with aqueous saturated sodium bicarbonate (15 ml). The solid dissolved and after separation, the aqueous layer was extracted with methylene chloride (5 ml). The methylene chloride solutions were combined, washed with water (10 ml), dried over sodium sulfate, and evaporated to a white foam which was crystalized from chloroform-methanol; white prisms; mp 260°–262° C. dec (lit.: Currie et al J. Chem. Soc. 4693 (1961) 254°–255° C.); yield 0.94 g (92%); tlc: single spot of $R_f$ 0.42.

IR($\mu$): 2.94 3.14 (m), 3.54 (w), 5.79 (s), 6.05–6.25 (s, 6.16 max.); $CH_2Cl_2$.

NMR($\delta$): 6.8–6.5 (m), 5.2–4.9 (broad), 4.7–1.3 (m, with small spike at 4.64 and large spikes at 3.89 and 2.15); ratio 2:1:18; $CDCl_3$.

MS(m/e): 343.1425 (P, 100%, Calc. 343.1419), 258.0877 (P-$CH_2CH_2NCOCH_3$, 53%, Calc. 258.0891), 239 (52%), 201 (66%).

Similarly 3,14-diacetylnoroxymorphone hydrochloride was converted to 3,N-diacetylnoroxymorphone.

IR($\mu$): 2.91–3.15 (m), 5.65 (s), 5.74 (s), 6.1–6.25 (s); $CH_2Cl_2$.

EXAMPLE II

CYCLOBUTYL CARBINOL

This was prepared from cyclobutanecarboxylic acid (Aldrich) and lithium aluminum hydride (Ventron) according to Pines; bp 140°–141.5° C. (Pines, et al. J.A.C.S., 75, 6065 (1953): 142°–143.5° C.).

NMR($\delta$): 3.83 (s), 3.53 (d, J = 6), 2.8–1.4 (m); ratio 1:2:7; $CDCl_3$.

EXAMPLE III

CYCLOBUTYLCARBINYL BROMIDE

Cyclobutyl carbinol was treated with phosphorous tribromode according to Mizzoni's procedure; bp 134°–135° C. (Mizzoni and deStevens, U.S. Pat. No. 3,385,857: 134°–136° C.).

NMR($\delta$): 3.38 (d, J = 7), 3.1–1.4 (m); ratio 2:7; $CCl_4$.

EXAMPLE IV

N-CYCLOBUTYLMETHYLNOROXYCODONE (6b) FROM NOROXYCODONE

The cmpound was prepared by a method analogous to Blumberg's synthesis (U.S. Pat. No. 3,332,950) of N-cyclobutylmethylnoroxymorphone. A solution of noroxycondone (6.88 g, 0.023 mole) and cyclobutylcarbinyl bromide (6.81 g, 0.046 mole) in dimethylformamide (275 ml) was heated with stirring (under nitrogen) for one week at 70° C. The solvent and excess alkyl bromide were removed in vacuo and the oily brown product then was taken up in chloroform (50 ml). This solution was washed with saturated aqueous sodium carbonate (30 ml) and water (30 ml), then dried over sodium sulfate and concentrated to ca. 25 ml. Some of the brown color ws removed by passage through a short silica gel 60 column (chloroform as eluant). Vacuum evaporation of the total eluate gave a brown foam which was crystalized from ether-hexane; pale yellow solid of mp 96°–97.5° C.; yield 2.82 g (34%); tlc: single spot of $R_f$ 0.63 (solvent A). Though the color and mp indicated that the sample was less pure, this product was spectroscopically idential to the material from the lithium aluminum hydride reduction, vida infra (mixed mp also undepressed).

When noroxycodone was treated with cyclobutylcarbinyl bromide in 1:1 95% ethanol-chloroform using conditions previously described for the similar alkylation with cyclopropylcarbinyl bromide, a mixture of products (at least five tlc spots) was obtained.

EXAMPLE V

N-CYCLOBUTYLCARBONYLNOROXYCO-DONE (2b)

A solution of 14-cyclobutylcarbonylnoroxycodone hydrochloride (1b) (1.68 g, 0.004 mole) in methylene chloride (20 ml) was vigorously shaken for 10 minutes with aqueous saturated sodium bicarbonate (15 ml). After separation, the aqueous layer was extracted with more methylene chloride (5 ml). The total extract then was washed with water (5 ml), dried over sodium sulfate, and evaporated to give N-cyclobutylcarbonyl-noroxycodone (2a) as a white foam; yield 1.49 g (97%); tlc: single spot of $R_f$ 0.49.

Although this compound could not be obtained; in crystalline form, a sample was prepared for elemental analysis by eluting a chloroform solution through a short silica gel 60 column. Evaporation of the total eluate gave a foam which was dried at 70° C. at one torr for two days. The combustion analysis was correct if the presence of ca. 0.1 equivalent of chloroform was assumed (confirmed by NMR analysis). If the evacuation process was prolonged or if a higher drying temperature was used, decomposition occurred. Combustion analysis indicated the presence of some chlorine in the partly decomposed samples.

Calc. for $C_{22}H_{25}NO_5$: C, 68.91%; H, 6.57%; N, 3.65%. + 0.1 $CHCl_3$: C, 67.13%; H, 6.40%; N, 3.54%. Found: C, 67.16%; H, 6.74%; N, 3.37%.

IR($\mu$) 2.92–3.12 (m), 3.52 (sh), 3.56 (w), 5.78 (s), 6.07–6.28 (s, 6.20 max.); $CH_2Cl_2$.

NMR($\delta$): 6.7–6.2 (m), 5.1–1.1 (m, with small spike at 4.46 and large spike at 3.86; ratio 2:23; $CCl_4$; chloroform at 7.23 (s).

MS(m/e): 383.1724 (P, 72%, Calc. 383.1732), 327 (10%), 301 (14%), 258 (49%), 239 (33%), 228 (33%), 201 (51%), 185 (26%), 55 (100%).

In accordance with the above procedure, but where, in place of 14-cyclobutylcarbonylnoroxycodone hydrochloride, there are used the acid salts of 14-cyclopropylcarbonylnoroxycodone (1a), 14-cyclopropylcarbonyloxy-3-methoxymorphinan (1e), or 14-cyclobutylcarbonyloxy-3-methoxy-6-oxomorphinan (1f), there is obtained the corresponding N-cyclopropylcarbonyl-noroxycodone (2a) (tlc: single spot of $R_f$ 0.49), IR($\mu$): 2.91–3.13 (m), 3.51 (sh), 3.55 (w), 5.79 (s), 6.07–6.33 (s, max at 6.23); $CH_2Cl_2$.

NMR($\delta$): 7.1–6.7 (m), 5.3–3.9 (m with small spike at 4.81 and large spike at 4.01), 3.8–0.5 (m); ratio 2:7:14; $CDCl_3$ (some $CHCl_3$ at 7.50). 14-hydroxy-N-cyclopropylcarbonyl-3-methoxymorphinan (2e), and 14-hydroxy-N-cyclobutylcarbonyl-3-methoxy-6-oxomorphinan (2f).

Essentially quantitative formation of N-cyclobutylcarbonylnoroxycodone (2b) was found when 14-cyclobutylcarbonylnoroxycodone hydrochloride (1b) was treated with bases under the following conditions (all at room temperature):

(1b) dispersed in benzene or ether was shaken in a separatory funnel with aqueous sodium bicarbonate; (2b) was isolated by separation and evaporation of the organic phase.

(1b) in chloroform or methylene chloride was shaken in a separatory funnel with aqueous solutions of pyridine or triethylamine; (2b) was isolated by separation and evaporation of the organic phase.

(1b) was dissolved in water and excess ammonium hydroxide or a single equivalent of sodium hydroxide or potassium hydroxide was added; (2b) was isolated by immediate extraction with chloroform followed by evaporation of the organic solvent.

(1b) was dissolved in ethanol-free chloroform and excess triethylamine or 1,8-bis-dimethylaminonaphthalene was added; IR analysis showed that (1b) was completely converted to (2b) after an hour; (2b) was isolated by extraction with water followed by evaporation of the chloroform layer.

(1b) in ethanol was shaken with an equivalent of the ion exchange resin Amberlite IRA-400 (Mallinckrodt) in the hydroxide form for five minutes; the resin was removed by decantation and (2b) was isolated by evaporation of the ethanol.

In another experiment, (1b) was converted to the nitrate salt by adding one equivalent of silver nitrate and 0.02 equivalents of nitric acid to a solution in water. The precipitated silver chloride was removed by filtration. Aqueous sodium bicarbonate was added to the nitrate salt partitioned between chloroform and water. (2b) was isolated by separation of the layers followed by evaporation of the chloroform. In similar experiments, the perchlorate and acetate salts of (1b) was made by adding silver perchlorate (plus 0.01 equivalents of perchloric acid) and silver acetate (plus 0.20 equivalents of acetic acid), respectively, to solutions of (1b) in water followed by filtration of the precipitated silver chloride. These salts were also converted to (2b) as described above.

In another experiment, sodium acetate trihydrate (68 mg, 0.5 m.mol) was added to a solution of (1b) (0.21 g, 0.5 m.mol) in 10 ml of water. On warming the solution a gum (presumably 2b) precipitated. After 20 minutes at 40° C. precipitation ceased and the gum was extracted into methylene chloride. The organic extract was dried over sodium sulfate and evaporated in vacuum (ultimately at 1 torr and 60°) to remove the last traces of solvent and acid. The residue (0.18 g) had the same physical, chromatographic, ad spectral properties as the (2b) obtained in the first experiment above. Addition of a few drops of aqueous sodium bicarbonate to the aqueous layer from the above extraction caused that solution to become cloudy. A further trace of (2b), less than 10 mg, was obtained by similar extraction of this solution with methylene chloride.

EXAMPLE VI n-CYCLOBUTYLCARBONYLNOROXYCO-DONE-6-ETHYLENE KETAL (3b) (From N-VOC-14-Cyclobutylcarbonylnoroxycodone Without isolation of Intermediates (i) Hydrogen chloride (Matheson, technical, passed through calcium chloride) was vigorously bubbled (35 cc per minute) through a stirred solution of unpurified N-VOC-14-cyclobutylcarbonylnoroxycodone (9″b) (10.72 g, 0.0236 mole) in methylene chloride (200 ml) for 2.5 hours. The solvent was removed in vacuo and the tan foam was then refluxed for one hour in absolute methanol (200 ml). Evaporation of this solution gave a tan, granular solid which was vacuum dried (0.3 torr) for an hour. This unpurified 14-cyclobutylcarbonylnoroxycodone hydrochloride (1b) was mixed with chloroform (175 ml) and then thoroughly washed with saturated aqueous sodium bicarbonate (100 ml). After separation, the aqueous layer was extracted with more chloroform (30 ml). The total chloroform solution then was washed with water (40 ml), dried over sodium sulfate, and evaporated at reduced pressure to a tan foam.

A benzene solution (100 ml) of this unpurified N-cyclobutylcarbonylnoroxycodone (2b), ethylene glycol (Baker) (15.0 g, 0.234 mole), and anhydrous p-toluenesulfonic acid (0.25 g) was vigorously stirred under reflux for 36 hours. Water, which formed in the ketalization, was removed during this period with the aid of a Barrett moisture test receiver. Saturated aqueous sodium bicarbonate (25 ml) was added to the cooled reaction mixture which was then transferred to a separatory funnel where it was diluted with water (50 ml). Hot benzene (100 ml) was poured into the funnel and the mixture was shaken strenuously. After separation, the aqueous layer was further extracted with hot benzene (75 ml). This was then combined with the main organic extract and the total solution was washed with water (75 ml), warmed to 65° C. (necessary to prevent crystallization), dried over potassium carbonate, and evaporated to a pale yellow solid (11.35 g) which was recrystalized from hot benzene (60 ml); froths at 120°–130° C. (rapid heating), partially resolidifies at 150°–160° C., and then completely melts at 192°–192.5° C.; tlc: single spot of $R_f$ 0.47; weight 9.46 g. Upon concentration of the filtrate, two more crops of tlc-pure crystals were obtained; weight 0.85 g. All three samples were assayed by NMR to be a 1:1 complex of benzene and the ketal (4b).

NMR(δ): 7.28 (s), 6.8–6.4 (m), 5.1–4.8 (broad), 4.6–1.1 (m, with small spike at 4.54 and large spike at 3.83); ratio 6:2:1:26; CDCl$_3$.

In accordance with the above procedures, but, where in place of benzene, there is used as solvent o-, m-, or p-xylene (or mixtures thereof) toluene or mesitylene, there is obtained a corresponding complex.

(ii) Overnight vacuum drying of the 1:1 complex (4b) (0.4 torr and 90° C.) of the first crop gave N-cyclobutylcarbonylnoroxycodone-6-ethylene ketal (3b) as white needles; mp 191°–192° C.; yield 8.06 g (80%).

Upon similar treatment, the second crop also gave white needles; mp 190°–191.5° C.; yield 0.63 g (6%); whereas the third crop was obtained as an off-white power; mp 188.5°–190.5° C.; yield 0.10 g (1%). The filtrate residue (0.98 g) contained ca. 20–30% product (NMR assay). The analysis sample was recrystallized from methanol; mp 192.5°–193° C.

Calc. for $C_{24}H_{29}NO_6$: C, 67.43%; H, 6.84%; N, 3.28%. Found: C, 67.33%; H, 6.64%; N, 3.46%. IR(μ): 3.00 (w), 3.44 (m), 3.49 (m), 3.56 (w), 6.04–6.30 (s); $CH_2Cl_2$.

NMR(δ): 6.9–6.5 (m), 5.1–4.8 (broad), 4.6–1.1 (m, with small spike at 4.54 and large spike at 3.87); ratio 2:1:26; CDCl$_3$.

MS(m/e) 427.1983 (P, 26%, Calc. 427.1993), 310.1445 (P-$C_5H_9O_3$, 31%, Calc. 310.1443), 302.1158 (P-cyclobutyl-CONCH$_2$CH$_2$, 29%, Calc. 302.1153), 228 (27%), 198 (25%), 100 (32%), 99 (100%), 55 (94%).

In accordance with the above procedure, but starting with any of the other aryl solvent complexes set forth in section (i) supra, there is obtained the same product.

The vacuum dried (at 90° C.) N-cyclobutylcarbonylnoroxycodone-6-ethylene ketal dissolved in hot toluene and cooled gave a toluene adduct with similarly useful crystallization properties; m.p. (froth) at 115°–130° C., resolidified and melted at 192°–192.5° C. NMR analysis (of initial crystals) indicated that this material contained somewhat more than 0.5 equivalents of toluene per equivalent of ketal. Where tetrahydrofuran was used as the crystallization solvent, a tetrahydrofuran adduct was isolated; m.p. (froth) 115°–130° C., resolidify, m.p. 192°–192.5° C. NMR analysis indicated that this adduct contained somewhat more than one equivalent of tetrahydrofuran per equivalent of the ketal.

The ketal also gave adducts with methylene chloride (solvent:ketal ratio ca 0.5:1), chloroform (ca 0.2:1), dioxane (ca 0.3:1), and methanol (ca 0.25:1). However, these adducts lost solvent without significant frothing on heating and were also soluble enough in their respective solvents to afford no advantages as part of a purification procedure.

In accordance with the above procedures of sections (i) and (ii) hereof, but starting with the corresponding N-VOC-14-cyclopropylcarbonylnoroxycodone (9″a) or N-VOC-14-acetyl noroxycodone (9″c), N-VOC-14-cyclobutylcarbonyloxy-3-methoxy-6-oxomorphinan (9″f), there is obtained the corresponding N-cyclopropylcarbonylnoroxycodone-6-ethylene ketal (3a), N-acetylnoroxycodone-6-ethylene ketal (3c) or N-cyclobutylcarbonyloxy-3-methoxy-14-hydroxymorphinan-6-ethylene ketal (3f).

EXAMPLE VII

N-CYCLOBUTYLCARBONYLNOROXYCO-DONE-6-ETHYLENE KETAL (From N-[2,2,2-Trichloroethoxycarbonyl]-14-CYCLOBUTYLCARBONYLNOROXYCODONE Without Isolation of Intermediates Unpurified N-[2,2,2-trichloroethoxycarbonyl]-14-cyclobutylcarbonylnoroxycodone (9′b) (1.36 g. containing ca. 10% 2,2,2-trichloroethyl chloroformate) (0.0022 mole) was dissolved in aqueous 90% acetic acid (45 ml). Zinc dust (Fisher) (1.44 g, 0.022 mole) was added in six portions at 10 minute intervals and the mixture then was stirred for three hours. After filtration, the filtrate was taken to ca. pH 11 with aqueous 6 M sodium hydroxide (ice bath) and the resulting suspension was extracted with methylene chloride (5 × 50 ml). The extract was washed with water (40 ml), dried over sodium sulfate, and evaporated to a pale yellow foam (0.94 g); tlc: major spot with $R_f$ of 0.49 (N-cyclobutylcarbonylnoroxycodone) (2b) with a trace at $R_f$ 0.68 (N-[2,2,2-trichloroethoxycarbonyl]-14-cyclobutylcarbonylnoroxycodone).

In accordance with the above procedure, but starting with the corresponding N-[2,2,2-trichloroethoxycarbonyl]-14-cyclopropylcarbonylnoroxycodone (9'a), there is similarly produced N-cyclopropylcarbonyl-noroxycodone (2a) in essentially a quantitive yield from oxycodone (N-haloalkoxycarbonyl compound prepared in accordance with procedure in copending application RC 3.0-138).

A mixture of unpurified N-cyclobutylcarbonylnoroxycodone, ethylene glycol (1.36 g, 0.022 mole), and p-toluenesulfonic acid (0.10 g) in benzene (15 ml) was refluxed for 40 hours. Water which formed during the ketalization process was removed with a moisture trap. Next, aqueous saturated sodium bicarbonate (3 ml) was added, and the reaction mixture was transferred to a separatory funnel where it was diluted with hot benzene (15 ml) and water (5 ml). After separation, the aqueous layer was extracted with more hot benzene (15 ml) and the total benzene solution was warmed (necessary to prevent crystallization), washed with water (15 ml), warmed again, and then dried over potassium carbonate. Solvent evaporation afforded a light brown solid which was recrystalized from boiling benzene to yield N-cyclobutylcarbonylnoroxycodone-6-ethylene ketal benzene adduct (4b) as white needles; wt. of first crop 0.77 g; wt. of second crop 0.03 g. When heated rapidly, both fractions frothed at 120°–130° C., partially resolidified at 150°–160° C., and then remelted at ca. 185° C. Overnight vacuum drying (90° C. at 0.3 torr) removed the benzene of crystalization to give the pure ketal (5b); mp first crop 189°–190° C.; yield 0.65 g (77%); tlc: single spot of $R_f$ 0.47; mp second crop 183.5°–186° C.; yield 0.03 g (4%); tlc: single spot of $R_f$ 0.47. The filtrate residue (0.18 g) appeared to be mostly unreacted N-[2,2,2-trichloroethoxycarbonyl]-14-cyclobutylcarbonylnoroxycodone.

In accordance with the above procedure but starting with N-cyclopropylcarbonyloxycodone (2a), there is obtained the corresponding ketal benzene adduct (4a) and ketal (5a).

In accordance with the procedures of both of the foregoing steps but starting with N-(2,2,2-trichloroethoxycarbonyl) 14-cyclobutylcarbonyloxy-6-oxomorphinan prepared in accordance with the procedures of copending application, RC 3.0-138, there is obtained the corresponding N-cyclobutylcarbonyl-14-hydroxymorphinan-6-ethylene ketal and the benzene adduct thereof.

EXAMPLE VIII

N-ACETYLNOROXYCODONE-6-METHYL ENOL ETHER (3"c)

A solution of N-acetylnoroxycodone (2c) (0.34 g, 0.001 mole), trimethyl orthoformate (Aldrich) (0.16 g, 0.0015 mole), and p-toluenesulfonic acid (Fisher) (20 mg) in absolute methanol (5 ml) was stirred under nitrogen for 18 hours at 60° C. A distilling head was attached to the flask and over the next three hours, the temperature was slowly raised to 78° C. During this period, the solvent and other volatiles distilled away and at the end, only a white solid residue remained. This was dissolved in methylene chloride (10 ml), washed with aqueous saturated sodium bicarbonate (3 ml) and water (3 ml), dried over potassium carbonate, and evaporated to a white foam; yield 0.32 g (89%). The product was crystalized to yield N-acetylnoroxycodone-6-methyl enol ether (3"c) from methanol-pentane; mp 260.5°–262.5° C. dec.

IR($\mu$): 2.82 (w), 3.56 (w), 6.02–6.24 (s, 6.13 max.); $CH_2Cl_2$.

NMR($\delta$): 6.9–6.5 (m), 5.2–1.3 (m, with small spike at 4.86, triplet at 4.69, and large spikes at 3.87, 3.55, and 2.16); ratio 2:21; $CDCl_3$.

MS(m/e): 357.1543 (P, 66%, Calc. 357.1575, 216 (100%), 112 (62%).

EXAMPLE IX

N-ETHYLNOROXYCODONE (6c)

A solution of N-acetylnoroxycodone-6-methyl enol ether (0.25 g, 0.00076 mole) in dry tetrahydrofuran (5 ml) was slowly added (10 minutes) to a stirred suspension of lithium aluminum hydride (Ventron) (0.076 g, 0.002 mole) in tetrahydrofuran (10 ml). After 18 hours at room temperature and heating for 1.5 hours under reflux, the excess hydride was decomposed by the successive additions of water (0.1 ml), aqueous sodium hydroxide (15%, 0.1 ml), and more water (0.5 ml). After filtration, the solution was washed with aqueous saturated ammonium chloride (15 ml), dried over sodium sulfate, and evaporated to a white foam. This was dissolved in 1 N hydrochloric acid (20 ml) and heated for 2.5 hours at 95°–100° C. The cooled solution was basified (pH 11) with concentrated aqueous ammonium hydroxide and then extracted with methylene chloride (5 × 15 ml). The total extract was dried over sodium sulfate and evaporated to a tan solid; yield 0.14 g (61%). The product was recrystalized from ethanol to give N-ethylnoroxycodone (6c) as off-white needles; mp 193.5°–195.5° C.; tlc: single spot of $R_f$ 0.42.

IR($\mu$): 2.94–3.09 (m), 3.57 (m), 5.80 (s), 6.13 (w), 6.22 (m); $CH_2Cl_2$.

NMR($\delta$): 6.8–6.4 (m), 5.2–4.3 (broad, with small spike at 4.64), 3.90 (s), 3.4–1.3 (m), 1.12 (t, J = 7); ratio 2:2:3:13:3; $CDCl_3$.

MS(m/e) 329.1633 (P, 47%, Calc. 329.1627), 314.1406 (P-methyl, 46%, Calc. 314.1392), 244 (42%), 58 (100%).

EXAMPLE X

N-CYCLOBUTYLMETHYLNOROXYCODONE (6b)

(i) A suspension of lithium aluminum hydride (0.53 g, 0.014 mole) in freshly distilled tetrahydrofuran (100 ml) was stirred under nitrogen for one hour. Next, N-cyclobutylcarbonylnoroxycodone-6-ethylene ketal (3b) (2.99 g, 0.007 mole) in tetrahydrofuran (50 ml) was slowly dripped (30 minutes) into the stirred suspension which was then left at room temperature for 18 hours. After an hour's heating under reflux, the excess hydride was quenched by the successive additions of water (0.5 ml), aqueous sodium hydroxide (15%, 0.5 ml), and more water (1.5 ml). The solids were filtered off and washed with fresh tetrahydrofuran (100 ml) to give a clear, colorless filtrate which was then evaporated to a white solid residue of N-cyclobutylmethylnoroxycodone-6-ethylene ketal (5b) which is not further purified.

In accordance with the above procedure, but starting with N-cyclopropylcarbonyl-3-methoxy-14-hydroxymorphinan (2e), there is obtained the corresponding N-cyclopropylmethyl-3-methoxy-14-hydroxymorphinan (6e).

(ii) The ketal (5b) was dissolved in hydrochloric acid (1 N, 40 ml) and the solution was heated for two hours on a steam bath. After basification with concentrated aqueous ammonium hydroxide, the solution was extracted with methylene chloride (4 × 30 ml). The combined extract was washed with water (2 × 30 ml), dried over sodium sulfate, and evaporated at reduced pressure to an off-white foam. This was dissolved in chloroform (10 ml) and eluted through a short silica gel 60 column (chloroform as eluant) where all the color was removed. Concentration of the total eluate gave a pure white foam which was crystalized from ether-pentane to yield N-cyclobutylmethylnoroxycodone (6b); mp 98°–98.5° C.; yield 1.88 g (73%); tlc: single spot of $R_f$ 0.63. By concentration of the filtrate, a second crop of white crystals was obtained; mp 97.5°–98° C.; yield 0.31 g (12%); tlc: single spot of $R_f$ 0.63. The tlc of the filtrate residue (0.12 g) showed four spots with $R_f$s of 0.46 (small), 0.54 (trace), 0.63 (large), and 0.79 (large) (solvent A). The mp of the analysis sample was 97.8°–98.8° C.

Calc. for $C_{22}H_{27}NO_4$: C, 71.52%; H, 7.37%; N, 3.79%. Found: C, 71.67%; H, 7.24%; N, 3.65%. IR(μ): 2.93–3.07 (m), 3.56 (m), 5.79 (s), 6.13 (w), 6.22 (m); $CH_2Cl_2$ NMR(δ): 6.8–6.4 (m), 5.2–4.8 (broad), 4.59 (s), 3.89 (s), 3.4–1.1 (m); ratio 2:1:1:3:20; $CDCl_3$.

MS(m/e): 369.1932 (P, 18%, Calc. 369.1939), 314.1372 (P-cyclobutyl, 100%, Calc. 314.1392).

In accordance with the above procedures, but starting, in place of N-cyclobutylcarbonylnoroxycodone-6-ethylene ketal (3b), with N-cyclopropylcarbonylnoroxycodone-6-ethylene ketal (3a), N-acetylnoroxycodone-6-ethylene ketal (3c), or N-cyclobutylcarbonyl-3-methoxy-14-hydroxy-6-oxomorphinan-6-ethylene ketal (3f), there is obtained the corresponding N-cyclopropylmethylnoroxycodone (6a) (m.p. 97.5°–98.5° C.), N-ethylnoroxycodone (6c), and N-cyclobutylmethyl-3-methoxy-14-hydroxy-6-oxomorphinan (6f).

EXAMPLE XI

N-CYCLOBUTYLMETHYLNOROXYMORPHONE (7b)

N-cyclobutylmethylnoroxycodone (6b) (1.85 g, 0.005 mole) and pyridine hydrochloride (5.78 g, 0.05 mole) were throughly mixed in a 25 ml flask equipped with a stir bar and a short path distillation head. The flask was immersed in an oil bath and heated under nitrogen with stirring to 190° C. and left at that temperature for 20 minutes. Next, the temperature was raised to 200° C. over a five minute period and kept there for five minutes. A small amount of pyridine distilled over during the heating process. The reaction vessel was withdrawn from the oil bath; and when cool, the semisolid reaction mass was dissolved in water (60 ml). This solution was taken to ca. pH 9 with concentrated aqueous ammonium hydroxide thereby precipitating a solid which was extracted into ether (4 × 40 ml). The ether solution was extracted first with aqueous pH 13.1 sodium hydroxide (3 × 50 ml) and then with water (50 ml). (Unreacted N-cyclobutylmethylnoroxycodone, 0.21 g (11%), mp 96.5°–97.5° C., was recovered from the ether solution by concentration and recrystallization from ether-pentane.) Next, the pH of the combined aqueous extracts was lowered to 8.8 with aqueous 20% hydrochloric acid and the precipitated product was extracted into methylene chloride (6 × 50 ml). Then the methylene chloride solution was washed with water (75 ml), dried over sodium sulfate, and concentrated to a light brown solid. This was dissolved in hot chloroform (10 ml) and passed through a short silica gel 60 column (hot chloroform as eluant) where the brown color was removed. Evaporation of the total eluate gave an off-white solid which was recrystalized to yield, from ether, N-cyclobutylmethylnoroxymorphone (7b) as white needles which almost completely melted at 156.5°–157° C. (lit.: Blumberg supra 151°–152° C.) then partly resolidified and melted at 171.5°–172° C.; yield 1.16 g (65%); tlc: single spot of $R_f$ 0.46. Concentration of the filtrate afforded a second crop; mp 156°–156.5° C. then similarly at 170.5°–171° C.; yield 0.10 g (6%); tlc: single spot of $R_f$ 0.46. The filtrate residue (0.06 g) also showed a single tlc spot of the same $R_f$.

When this compound was precipitated from a chloroform solution by addition of pentane, the mp was 173°–174° C. Subsequent recrystalization from ether of the pentane precipitated material afforded white needles which again exhibited the earlier dual melting point behavior.

Calc. for $C_{21}H_{25}NO_4$: C, 70.96%; H, 7.09%; N, 3.94%. Found: C, 71.23%; H, 6.86%; N, 3.92%. Ir(μ): 2.84 (w), 2.92–3.16 (m), 3.53 (w), 3.57 (m), 5.81 (s), 6.10 (w), 6.19 (m); $CH_2Cl_2$.

NMR(δ): 6.8–6.4 (m), 6.2–5.8 (broadened s), 4.69 (s), 3.4–1.2 (m); ratio 2:2:1:20; $CDCl_3$.

MS(m/e): 355.1779 (P, 17%, Calc. 355.1784), 300.1255 (P-cyclobutyl, 100%, Calc. 300.1235), 243 (10%), 41 (43%).

In accordance with the above procedure, but starting, in place of N-cyclobutylmethylnoroxycodone, with N-cyclopropylmethylnoroxycodone (6a), N-ethylnoroxycodone (6c), N-cyclopropylmethyl-3-methoxy-14-hydroxymorphinan (6e), or N-cyclobutylmethyl-3-methoxy-14-hydroxy-6-oxomorphinan (6f), there is obtained the corresponding N-cyclopropylmethylnoroxymorphone (7a), N-ethylnoroxymorphone (7c), N-cyclopropylmethyl-3,14-dihydroxymorphinan (7e) or N-cyclobutylmethyl-3,14-dihydroxy-6-oxomorphinan (7f).

EXAMPLE XII

REACTION OF N-VOC-14-CYCLOBUTYLCARBONYLNOROXYCODONE WITH SODIUM HYDROXIDE

A solution of N-VOC-14-cyclobutylcarbonylnoroxycodone (9"b) (1.10 g, 0.0024 mole) in 1:1 dioxane-aqueous 0.1 M sodium hydroxide (50 ml) (0.0025 mole) was heated under nitrogen with stirring for four hours at 60° C. Next, carbon dioxide was bubbled through the stirred solution until the pH had dropped to ca. 7.5 (20 minutes). Removal of the solvent at reduced pressure afforded a yellow residue which was partioned between ethyl acetate (60 ml) and water (80 ml). After separation, the aqueous layer was extracted with more ethyl acetate (60 ml) and the total organic extract was washed with 0.3 N hydrochloric acid (30 ml), water (30 ml), aqueous 1% sodium bicarbonate (30 ml), and water (30 ml). The dried solution was evaporated to a yellow foam (0.79 g); tlc: two stops with $R_f$s of 0.49 and 0.74. A portion (0.36 g) of this material was chromatographed on eight silica preparative tlc plates (20 × 20 cm) using 9:1 methylene chloride-methanol as the eluant.

The $R_f$ 0.49 compound was desorbed with 20:1 chloroform-ethanol and recovered as a pale yellow oil (0.23 g) upon evaporation of solvent. Its IR and NMR spectra were identical to those of authentic -N-cyclobutylcarbonylnoroxycodone (2b).

EXAMPLE XIII

Formation of N-Phenoxycarbonyl-14-Cyclobutylcarbonylnoroxycodone (9"b) (By N-Demethylation of 14-Cyclobutylcarbonyloxycodone with Phenyl Chloroformate) and its Direct Conversion to N-Cyclobutylcarbonylnoroxycodone with Alkali A solution of 14-cyclobutylcarbonyloxycodone (1.194 g, 0.003 mole) and phenyl chloroformate (0.942 g, 0.006 mole) in 1,2-dichloroethane (8 ml) was heated at 70° C. for 67 hours and then at reflux for another 5 hours. Vacuum evaporation of the mixture was followed by extraction of an ethyl acetate solution (80 ml) of the reddish residue with water (25 ml), 0.3 N hydrochloric acid (25 ml), water (25 ml), 5% aqueous sodium carbonate (2 × 25 ml), and water (25 ml). The organic extract was then dried over anhydrous sodium sulffate and evaporated in vacuo to give a light yellow solid which was crystallized in three crops from hot ethyl acetate. Though this crystallized N-phenoxycarbonyl-14-cycloubtylcarbonylnoroxycodone (9"b) (mp 223°-228° C. dec corr.; 1.033 g; $R_f$ 0.73 vs. an oxycodone $R_f$ of 0.46) was contaminated with a little phenol and other minor impurities, these did not interfere in (and were easily removed in) the subsequent hydrolysis-rearrangement step.

IR(μ): 3.44 (m, broad), 3.56 (w), 5.75-5.9 (s, maxima at 5.78 and 5.85); CH$_2$Cl$_2$.

NMR(δ): 7.4-6.85 (m), 6.8-6.5 (m), 5.97-5.5 (broad), 4.8-3.7 (m with small spike at 4.63 and large spike at 3.87), 3.7-1.05 (m); ratio: 5:2:1:5:16; CDCl$_3$.

The thus produced N-phenoxycarbonyl-14-cyclobutylcarbonylnoroxycodone was heated with one equivalent of 0.2 N potassium hydroxide in 1:4 water-dioxane at 90° C. overnight. Concentration of the reaction mixture was followed by partitioning the residue between chloroform and water. The water layer next was washed with more chloroform. The combined chloroform extracts were washed with 0.3 N hydrochloric acid, 5% aqueous sodium carbonate, and water and then dried over anhydrous sodium sulfate and evaporated in vacuo to give N-cyclobutylcarbonylnoroxycodone (tlc: single spot $R_f$ 0.49) as a light yellow foam in over 90% yield. The IR and NMR spectra of this product were essentially identical to those of authentic N-cyclobutylcarbonylnoroxycodone. Tlc analysis of the aqueous extracts indicated that traces of noroxycodone had also been formed.

Substantially in accordance with the above, but starting with N-TOC-14-cyclobutylcarbonylnoroxycodone which is similarly reacted with 0.1 M aqueous sodium hydroxide (1.1 equivalents) in dioxane overnight and worked up there is produced N-cyclobutylcarbonyl-noroxycodone (2b) isolated by chromatography as above in Example XII.

EXAMPLE XIV

N-CYCLOPROPYLMETHYLNOROXYCODONE (6a) From N-CYCLOPROPYLCARBONYLNOROXYCODONE (2a)

The N-cyclopropylcarbonylnoroxycodone (from 3.45 g, 0.00827 mole, 14-cyclopropylcarbonylnoroxycodone hydrochloride, see Example V) was combined with redistilled ethylene glycol (5.51 g, 0.083 mole), p-toluene sulfonic acid (0.2 g) and benzene (50 ml) and vigorously stirred at reflux for 40 hours using a Barrett moisture test receiver to remove the water liberated. At this time the analysis indicated that some starting material remained so another 0.02 g of the toluene sulfonic acid catalyst was added and reflux was continued for another 41 hours. Saturated aqueous sodium bicarbonate (20 ml) was added to the cooled solution which was then transferred to a separatory funnel where the contents were diluted with 20 ml of water Hot benzene (50 ml) was also added and the mixture was shaken vigorously for two minutes. After separation, the aqueous layer was extracted with another 2 × 30 ml of hot benzene. The combined benzene extracts were washed with hot water (25 ml at 65° C.), dried over anhydrous potassium carbonate, and evaporated in vacuo (IR: no ketone absorption). The crude product was crystallized from 20 ml of hot benzene to give a benzene adduct of N-cyclopropylcarbonylnoroxycodone-6-ethylene ketal as white needles; m; 200°-201.5° C. corr.; weight 2.91 g; tlc: single spot of $R_f$ 0.62, NMR analysis indicated that the ratio of benzene to the ketal in the solid was ca 1.2:1. The crystallized filtrate was rotary evaporated and then left under high vacuum overnight. The residue, a tan foam (0.28 g), was mostly the desired product (NMR and tlc analysis). IR(μ): 2.87-3.1 (w), 3.44 (m), 3.49 (m), 3.57 (w), 6.08-6.3 (s); CH$_2$Cl$_2$.

NMR (δ): 7.1-6.6 (m), 5.2-0.5 (m with small spike at 4.65 and large spike at 3.95); ratio: 2:25; CDCk$_3$ (benzene spike at 7.47).

This benzene adduct of N-cyclopropylcarbonyl-noroxycodone-6-ethylene ketal (4a) (1.10 g) was heated at 90° C. (0.5 torr) for 2.5 hours, then diluted with dry tetrahydrofuran (20 ml), and added over a 15 minutes period to a stirred suspension of LiAlH$_4$ (0.17 g, 0.0046 mole) in tetrahydrofuran under a nitrogen atmosphere. After stirring overnight at room temperature and refluxing for an hour, the reduced ketal (5a) was worked up and hydrolyzed to (5a) as described as in Example X for the preparation of the cyclobutylmethyl analogue. N-Cyclopropylmethylnoroxycodone, initially obtained as an off-white foam on concentration of the silica gel 60 eluate, was crystallized from ether-pentane; mp 97.5°-98.5° C., corr; tlc: single spot of $R_f$ 0.54; yield 0.67 g. The spectral properties of this material were the same as those of the N-cyclopropylmethylnoroxycodone made by the process in the Applicant's copending application (RC 3.0-138).

The conversion, (2a) to (6a) was also performed in similar yield using crude (2a) made in essentially quantiative yield from (8a) by N-demethylation with 2,2,2-trichloroethylchloroformate to give N-trichloroethoxycarbonyl-14-cyclopropylcarbonylnoroxycodone (9'a) which was cleaved and rearranged to (2a) by the process in Example VII for the formation of (2b).

EXAMPLE XV

Thermal dissociation of N-trichloroethoxycarbonyl-14-cyclobutylcarbonyl-noroxycodone to N-cyclobutylcarbonylnoroxycodone N-trichloroethoxycarbonyl-14-cyclobutylcarbonyl-noroxycodone (9'b) (0.31 g) was heated under reflux in methanol (5 ml) containing 0.06 g zinc dust (1.9 eq) and 0.56 ml of 0.1 N aqueous hydrochloric acid (0.1 eq). The progress of the reaction and conversion to N-cyclobutylcarbonylnoroxycodone was followed by tlc analysis taking samples every hours. After three hours only a trace of the starting material remained, the main spot had the $R_f$ of N-cyclobutylcarbonylnoroxycodone and the only other significant UV sensitive spot was at the origin (the $R_f$ of the O-acyl salt). Solid sodium bicarbonate (0.1 eq) was then added, and the mixture was filtered to remove the excess zinc. The filtrate was evaporated and the residue was partitioned between water and chloroform. Aqueous sodium hydroxide was then added first to precipitate the zinc hydroxide and then with more base to dissolve it. The chloroform layer was then extracted with dilute aqueous hydrochloric acid, water, dried over sodium sulfate, and evaporated to give N-cyclobutylcarbonylnoroxycodone (2b) (0.22 g) contaminated by only traces of starting material and other impurities. These were readily removed by chromatography to give product whose physical and spectral properties were identical to those of the material obtained in Example V.

We claim:

1. A process of preparing a morphinan of formula

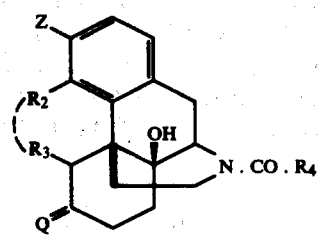

the corresponding optical isomer thereof and mixtures of said optical isomers which comprises adding to an acid addition salt selected from the group having the formula

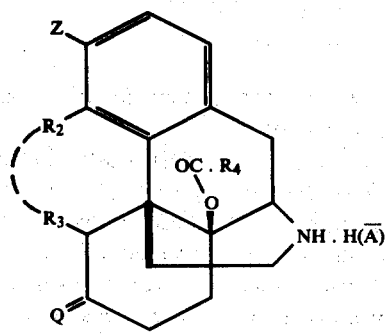

the corresponding optical isomer thereof or admixtures of said optical isomers, an amount of base sufficient to neutralize said acid salt wherein H(A) is a hydrogen acid capable of forming a salt with a secondary amine, wherein Z is $R_1O$, $R_1$ is lower alkyl or phenyl lower alkyl wherein the alkyl moiety contains 1 to 5 carbon atoms, straight or branch chain lower alkanoyl having 1 to 5 carbon atoms in the alkyl moiety thereof, or cycloalkylcarbonyl and substituted cycloalkylcarbonyl having 3 to 6 carbon atoms in the cyclic moiety thereof, benzoyl, substituted benzoyl, or phenylalkanoyl or substituted phenylalkanoyl of 1 to 6 carbon atoms in the alkanoyl moiety wherein the substituents are loweralkyl of 1-5 carbon atoms, $R_2$ and $R_3$ are hydrogen or when taken together $R_2$ and $R_3$ are oxa, Q is two hydrogen atoms or oxo, $R_4$ is hydrogen, straight or branch chain lower alkyl having 1 to 5 carbon atoms in the alkyl moiety thereof, cycloalkyl or substituted cycloalkyl having 3 to 6 carbon atoms in the cyclic moiety, phenyl, substituted phenyl, phenylalkyl or substituted phenylalkyl of 1 to 5 carbon atoms in the alkyl moiety, wherein the substituents are loweralkyl of 1-5 carbon atoms in the loweralkyl moiety thereof.

2. A process of preparing a morphinan selected from the group having the formula

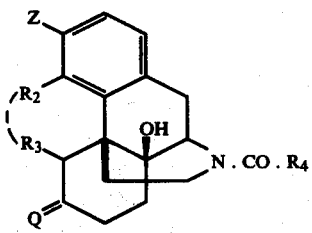

the corresponding optical isomer thereof and mixtures of said isomers, wherein Z, $R_1$, $R_2$, $R_3$, $R_4$ and Q is as defined in claim 1 which comprises treating a morphinan selected from the group having the formula

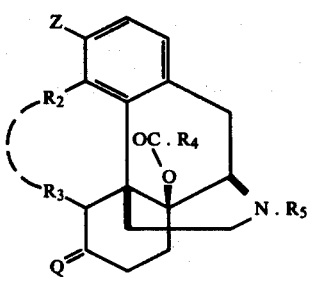

the corresponding optical isomer thereof and mixtures of said isomers, wherein $R_5$ is selected from the group consisting of trichloroethoxycarbonyl vinyloxycarbonyl and phenyloxycarbonyl with a base.

3. A process according to claim 2 wherein the base is an aqueous alkali.

4. A process of claim 1 wherein Z is $R_1O$ and $R_1$ is lower alkyl.

5. A process in accordance with claim 1 wherein the base is selected from the group consisting of alkali metal hydroxides, alkaline earth metal hydroxides, alkali metal carbonates, alkaline earth metal carbonates, and alkali metal bicarbonates, ammonium hydroxide, amines and ion exchange resins in the hydroxide form.

6. A process in accordance with claim 5 wherein the base is sodium bicarbonate.

7. A process of claim 4 wherein R₁ is methyl, R₂ with R₃ is oxa, Q ia oxo.

8. A process according to claim 7 wherein R₄ is selected from the group consisting of cyclopropyl and cyclobutyl.

9. The adduct of a compound having the formula

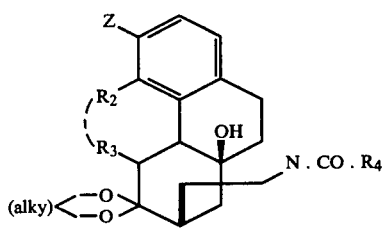

the corresponding optical isomer, and mixtures of said optical isomers, wherein Z, R₁ and R₄ are as defined in claim 1, provided R₁ is other than alkanoyl, R₂ with R₃ is oxa, and (alky) is alkylene of 2 to 5 carbon atoms in the alkylene moiety, with a member selected from the group consisting of benzene, loweralkyl and polyloweralkyl substituted benzenes, tetrahydrofuran and polyloweralkyl substituted tetrahydrofurans wherein the substituted benzene nucleus carries 1–6 substituents and the substituted furan nucleus carries 1–4 substituents and lower alkyl contains 1–5 carbon atoms.

10. The adduct of a compound of claim 9 wherein Z is R₁O, R₁ is methyl, R₄ is selected from the group consisting of cyclobutyl and cyclopropyl, and (alky) is ethylene and members selected from the group consisting of benzene, toluene and tetrahydrofuran.

11. A process of preparing a morphinan selected from the group having the formula

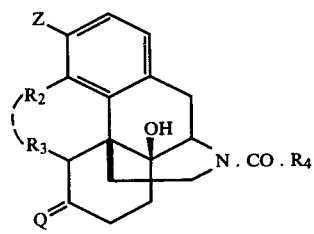

the corresponding optical isomer thereof and mixture of said optical isomers, wherein Z, R₁, R₂, R₃, R₄ and Q are as defined in claim 1 which comprises (a) reacting an O-acyl morphinan selected from the group having the formula

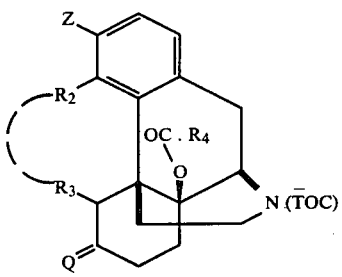

the corresponding optical isomer thereof and mixtures of said optical isomers, wherein (TOC) is selected from the group consisting of 2-haloethoxycarbonyl, 2,2-dihaloethoxycarbonyl, and 2,2,2-trihaloethoxycarbonyl wherein halo is chloro or bromo with zinc, or a zinc copper couple in a protic solvent selected from the group consisting of lower alkanoic acid, an aqueous lower alkanoic acid, a lower alkanol, aqueous lower alkanol, water, or a mixture of water with a reaction-inert water miscible co-solvent in the presence of substantially one or more equivalents of acid, and, (b) thereafter adding a sufficient amount of base to neutralize said acid.

12. A process according to claim 11 wherein Z is R₁O and (TOC) is trichloroethoxycarbonyl and the reaction medium is aqueous acetic acid.

13. A process according to claim 11 wherein the water miscible co-solvent is selected from the group consisting of dioxane, glyme, ethyleneglycol, and tetrahysrofuran.

14. A process comprising reacting an O-acyl morphinan selected from the group having the formula

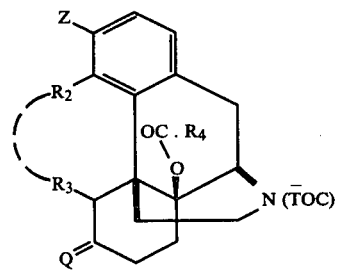

the corresponding optical isomer thereof and mixtures of said optical isomers, wherein Z, R₁, R₂, R₃, R₄, and Q are as defined in claim 1 and (TOC) is selected from the group consisting of 2-haloethoxycarbonyl, 2,2-dihaloethoxycarbonyl, and 2,2,2-trihaloethoxycarbonyl wherein halo is chloro or bromo with zinc, copper, or a zinc couple in (a) a lower alkanoic acid or aqueous lower alkanoic acid (b) removing the said acid under reduced pressure and heating the residue to provide a morphinan from the group having the formula

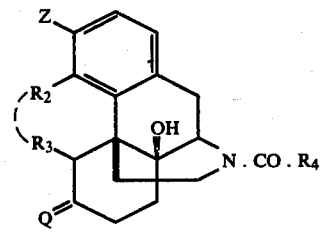

the corresponding optical isomer thereof and mixtures of said optical isomers.

15. A process according to claim 14 which comprises heating in a temperature range of 40° to 150° C.

16. A process comprising reacting an O-acyl morphinan selected from the group having the formula

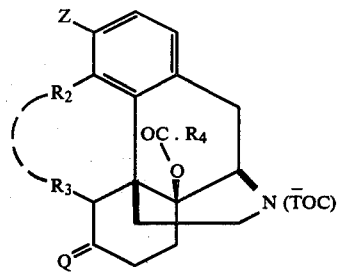

the corresponding optical isomer thereof and mixtures of said optical isomers, wherein Z, $R_1$, $R_2$, $R_3$, $R_4$, and Q are as defined in claim 1 and (TOC) is selected from the group consisting of 2-haloethoxycarbonyl, 2,2-dihaloethoxycarbonyl, and 2,2,2-trihaloethoxycarbonyl wherein halo is chloro or bromo with zinc, or a zinc copper couple in the presence of a small amount of acid, to provide a morphinan from the group having the formula the corresponding optical isomer thereof and mixtures of said optical isomers.

17. A process according to claim 16 comprising the additional step of adding a sufficient amount of base to neutralize the acid.

* * * * *